United States Patent
Komp et al.

(10) Patent No.: US 12,102,298 B2
(45) Date of Patent: Oct. 1, 2024

(54) LYMPHATIC SYSTEM TRACKING

(71) Applicant: Covidien LP, Mansfield, MA (US)

(72) Inventors: John W. Komp, Dillon, CO (US); Joe D. Sartor, Longmont, CO (US)

(73) Assignee: Covidien LP, Mansfield, MA (US)

( * ) Notice: Subject to any disclaimer, the term of this patent is extended or adjusted under 35 U.S.C. 154(b) by 415 days.

(21) Appl. No.: 17/072,753

(22) Filed: Oct. 16, 2020

(65) Prior Publication Data

US 2021/0169330 A1 Jun. 10, 2021

Related U.S. Application Data

(60) Provisional application No. 62/946,307, filed on Dec. 10, 2019.

(51) Int. Cl.
| | |
|---|---|
| *A61B 1/06* | (2006.01) |
| *A61B 1/00* | (2006.01) |
| *A61B 1/04* | (2006.01) |
| *A61B 5/00* | (2006.01) |
| *A61B 5/06* | (2006.01) |

(52) U.S. Cl.
CPC ...... *A61B 1/0638* (2013.01); *A61B 1/000094* (2022.02); *A61B 1/0002* (2013.01); *A61B 1/0005* (2013.01); *A61B 1/046* (2022.02); *A61B 5/0035* (2013.01); *A61B 5/0086* (2013.01); *A61B 5/062* (2013.01); *A61B 5/418* (2013.01); *A61B 1/06* (2013.01)

(58) Field of Classification Search
None
See application file for complete search history.

(56) References Cited

U.S. PATENT DOCUMENTS

| | | | |
|---|---|---|---|
| 5,057,494 | A | 10/1991 | Sheffield |
| 5,321,113 | A | 6/1994 | Cooper et al. |
| 6,003,517 | A | 12/1999 | Sheffield et al. |
| 8,335,359 | B2 | 12/2012 | Fidrich et al. |
| 8,706,184 | B2 | 4/2014 | Mohr et al. |
| 8,827,934 | B2 | 9/2014 | Chopra et al. |
| 9,375,268 | B2 | 6/2016 | Long |
| 9,918,659 | B2 | 3/2018 | Chopra et al. |
| 10,004,558 | B2 | 6/2018 | Long et al. |
| 10,194,897 | B2 | 2/2019 | Cedro et al. |

(Continued)

FOREIGN PATENT DOCUMENTS

| | | |
|---|---|---|
| BR | 0013237 A | 7/2003 |
| BR | 0116004 A | 6/2004 |

(Continued)

OTHER PUBLICATIONS

Extended European Search Report issued in European Application No. 20212737.9 dated Aug. 13, 2021, 13 pages.

(Continued)

*Primary Examiner* — Patrick Fernandes
*Assistant Examiner* — Marjan Saboktakin
(74) *Attorney, Agent, or Firm* — Weber Rosselli & Cannon LLP

(57) ABSTRACT

A system and method for imaging tissue including an endoscope capable of illuminating tissue with white and near infrared light. The method includes detecting the fluorescence and displaying the detected fluorescence in combination with white light images.

17 Claims, 5 Drawing Sheets

(56) References Cited

U.S. PATENT DOCUMENTS

| | | | |
|---|---|---|---|
| 10,373,719 B2 | 8/2019 | Soper et al. | |
| 10,376,178 B2 | 8/2019 | Chopra | |
| 10,405,753 B2 | 9/2019 | Sorger | |
| 10,478,162 B2 | 11/2019 | Barbagli et al. | |
| 10,480,926 B2 | 11/2019 | Froggatt et al. | |
| 10,524,866 B2 | 1/2020 | Srinivasan et al. | |
| 10,555,788 B2 | 2/2020 | Panescu et al. | |
| 10,569,071 B2 | 2/2020 | Harris et al. | |
| 10,603,106 B2 | 3/2020 | Weide et al. | |
| 10,610,306 B2 | 4/2020 | Chopra | |
| 10,638,953 B2 | 5/2020 | Duindam et al. | |
| 10,639,114 B2 | 5/2020 | Schuh et al. | |
| 10,674,970 B2 | 6/2020 | Averbuch et al. | |
| 10,682,070 B2 | 6/2020 | Duindam | |
| 10,702,137 B2 | 7/2020 | Deyanov | |
| 10,706,543 B2 | 7/2020 | Donhowe et al. | |
| 10,709,506 B2 | 7/2020 | Coste-Maniere et al. | |
| 10,772,485 B2 | 9/2020 | Schlesinger et al. | |
| 10,796,432 B2 | 10/2020 | Mintz et al. | |
| 10,823,627 B2 | 11/2020 | Sanborn et al. | |
| 10,827,913 B2 | 11/2020 | Ummalaneni et al. | |
| 10,835,153 B2 | 11/2020 | Rafii-Tari et al. | |
| 10,885,630 B2 | 1/2021 | Li et al. | |
| 2002/0147462 A1 | 10/2002 | Mair et al. | |
| 2003/0013972 A1 | 1/2003 | Makin | |
| 2004/0120981 A1 | 6/2004 | Nathan | |
| 2008/0045938 A1 | 2/2008 | Weide et al. | |
| 2010/0286529 A1 | 11/2010 | Carroll et al. | |
| 2011/0082369 A1 | 4/2011 | Mohr et al. | |
| 2013/0303945 A1 | 11/2013 | Blumenkranz et al. | |
| 2014/0024948 A1* | 1/2014 | Shida | A61B 1/00009 600/476 |
| 2014/0035798 A1 | 2/2014 | Kawada et al. | |
| 2014/0051986 A1 | 2/2014 | Zhao et al. | |
| 2015/0018690 A1 | 1/2015 | Kang et al. | |
| 2015/0148690 A1 | 5/2015 | Chopra et al. | |
| 2015/0265368 A1 | 9/2015 | Chopra et al. | |
| 2016/0157939 A1 | 6/2016 | Larkin et al. | |
| 2016/0183841 A1 | 6/2016 | Duindam et al. | |
| 2016/0192860 A1 | 7/2016 | Allenby et al. | |
| 2016/0262602 A1* | 9/2016 | Yu | A61B 1/00009 |
| 2016/0287344 A1 | 10/2016 | Donhowe et al. | |
| 2017/0112571 A1 | 4/2017 | Thiel et al. | |
| 2017/0112576 A1 | 4/2017 | Coste-Maniere et al. | |
| 2017/0209071 A1 | 7/2017 | Zhao et al. | |
| 2017/0265952 A1 | 9/2017 | Donhowe et al. | |
| 2017/0311844 A1 | 11/2017 | Zhao et al. | |
| 2017/0319165 A1 | 11/2017 | Averbuch | |
| 2018/0078318 A1 | 3/2018 | Barbagli et al. | |
| 2018/0144092 A1 | 5/2018 | Flitsch et al. | |
| 2018/0153621 A1 | 6/2018 | Duindam et al. | |
| 2018/0235709 A1 | 8/2018 | Donhowe et al. | |
| 2018/0240237 A1 | 8/2018 | Donhowe et al. | |
| 2018/0256262 A1 | 9/2018 | Duindam et al. | |
| 2018/0263706 A1 | 9/2018 | Averbuch | |
| 2018/0279852 A1 | 10/2018 | Rafii-Tari et al. | |
| 2018/0325419 A1 | 11/2018 | Zhao et al. | |
| 2019/0000559 A1 | 1/2019 | Berman et al. | |
| 2019/0000560 A1 | 1/2019 | Berman et al. | |
| 2019/0008413 A1 | 1/2019 | Duindam et al. | |
| 2019/0038365 A1 | 2/2019 | Soper et al. | |
| 2019/0065209 A1 | 2/2019 | Mishra et al. | |
| 2019/0110839 A1 | 4/2019 | Rafii-Tari et al. | |
| 2019/0175062 A1 | 6/2019 | Rafii-Tari et al. | |
| 2019/0175799 A1 | 6/2019 | Hsu et al. | |
| 2019/0183318 A1 | 6/2019 | Froggatt et al. | |
| 2019/0183585 A1 | 6/2019 | Rafii-Tari et al. | |
| 2019/0183587 A1 | 6/2019 | Rafii-Tari et al. | |
| 2019/0192234 A1 | 6/2019 | Gadda et al. | |
| 2019/0209016 A1 | 7/2019 | Herzlinger et al. | |
| 2019/0209043 A1 | 7/2019 | Zhao et al. | |
| 2019/0216548 A1 | 7/2019 | Ummalaneni | |
| 2019/0239723 A1 | 8/2019 | Duindam et al. | |
| 2019/0239831 A1 | 8/2019 | Chopra | |
| 2019/0250050 A1 | 8/2019 | Sanborn et al. | |
| 2019/0254649 A1 | 8/2019 | Walters et al. | |
| 2019/0269470 A1 | 9/2019 | Barbagli et al. | |
| 2019/0269818 A1 | 9/2019 | Dhanaraj et al. | |
| 2019/0269819 A1 | 9/2019 | Dhanaraj et al. | |
| 2019/0272634 A1 | 9/2019 | Li et al. | |
| 2019/0298160 A1 | 10/2019 | Ummalaneni et al. | |
| 2019/0298451 A1 | 10/2019 | Wong et al. | |
| 2019/0320878 A1 | 10/2019 | Duindam et al. | |
| 2019/0320937 A1 | 10/2019 | Duindam et al. | |
| 2019/0336238 A1 | 11/2019 | Yu et al. | |
| 2019/0343424 A1 | 11/2019 | Blumenkranz et al. | |
| 2019/0350659 A1 | 11/2019 | Wang et al. | |
| 2019/0365199 A1 | 12/2019 | Zhao et al. | |
| 2019/0365479 A1 | 12/2019 | Rafii-Tari | |
| 2019/0365486 A1 | 12/2019 | Srinivasan et al. | |
| 2019/0380787 A1 | 12/2019 | Ye et al. | |
| 2020/0000319 A1 | 1/2020 | Saadat et al. | |
| 2020/0000526 A1 | 1/2020 | Zhao | |
| 2020/0008655 A1 | 1/2020 | Schlesinger et al. | |
| 2020/0030044 A1 | 1/2020 | Wang et al. | |
| 2020/0030461 A1 | 1/2020 | Sorger | |
| 2020/0038750 A1 | 2/2020 | Kojima | |
| 2020/0043207 A1 | 2/2020 | Lo et al. | |
| 2020/0046431 A1 | 2/2020 | Soper et al. | |
| 2020/0046436 A1 | 2/2020 | Tzeisler et al. | |
| 2020/0054399 A1 | 2/2020 | Duindam et al. | |
| 2020/0054408 A1 | 2/2020 | Schuh et al. | |
| 2020/0060771 A1 | 2/2020 | Lo et al. | |
| 2020/0069192 A1 | 3/2020 | Sanborn et al. | |
| 2020/0077870 A1 | 3/2020 | Dicarlo et al. | |
| 2020/0078023 A1 | 3/2020 | Cedro et al. | |
| 2020/0078095 A1 | 3/2020 | Chopra et al. | |
| 2020/0078103 A1 | 3/2020 | Duindam et al. | |
| 2020/0085514 A1 | 3/2020 | Blumenkranz | |
| 2020/0109124 A1 | 4/2020 | Pomper et al. | |
| 2020/0129045 A1 | 4/2020 | Prisco | |
| 2020/0129239 A1 | 4/2020 | Bianchi et al. | |
| 2020/0138514 A1 | 5/2020 | Blumenkranz et al. | |
| 2020/0138515 A1 | 5/2020 | Wong | |
| 2020/0142013 A1 | 5/2020 | Wong | |
| 2020/0155116 A1 | 5/2020 | Donhowe et al. | |
| 2020/0155232 A1 | 5/2020 | Wong | |
| 2020/0170623 A1 | 6/2020 | Averbuch | |
| 2020/0170720 A1 | 6/2020 | Ummalaneni | |
| 2020/0179058 A1 | 6/2020 | Barbagli et al. | |
| 2020/0188021 A1 | 6/2020 | Wong et al. | |
| 2020/0188038 A1 | 6/2020 | Donhowe et al. | |
| 2020/0205903 A1 | 7/2020 | Srinivasan et al. | |
| 2020/0205904 A1 | 7/2020 | Chopra | |
| 2020/0214664 A1 | 7/2020 | Zhao et al. | |
| 2020/0229679 A1 | 7/2020 | Zhao et al. | |
| 2020/0242767 A1 | 7/2020 | Zhao et al. | |
| 2020/0275822 A1* | 9/2020 | Michihata | G06T 7/0012 |
| 2020/0275860 A1 | 9/2020 | Duindam | |
| 2020/0297442 A1 | 9/2020 | Adebar et al. | |
| 2020/0315554 A1 | 10/2020 | Averbuch et al. | |
| 2020/0322512 A1* | 10/2020 | Aono | A61B 1/045 |
| 2020/0330795 A1 | 10/2020 | Sawant et al. | |
| 2020/0352427 A1 | 11/2020 | Deyanov | |
| 2020/0364865 A1 | 11/2020 | Donhowe et al. | |
| 2020/0383750 A1 | 12/2020 | Kemp et al. | |
| 2021/0000524 A1 | 1/2021 | Barry et al. | |
| 2021/0059532 A1* | 3/2021 | Tsumatori | A61B 5/0084 |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CZ | 1644519 | 12/2008 |
| CZ | 486540 | 9/2016 |
| CZ | 2709512 | 8/2017 |
| CZ | 2884879 | 1/2020 |
| EP | 1644519 B1 | 12/2008 |
| EP | 2141497 A1 | 1/2010 |
| EP | 3413830 A4 | 9/2019 |
| EP | 3478161 A4 | 2/2020 |
| EP | 3641686 A2 | 4/2020 |
| EP | 3644885 A1 | 5/2020 |

(56) References Cited

FOREIGN PATENT DOCUMENTS

| | | |
|---|---|---|
| EP | 3644886 A1 | 5/2020 |
| EP | 3749239 A1 | 12/2020 |
| KR | 20190032758 A | 3/2019 |
| MX | PA03005028 A | 1/2004 |
| MX | PA03000137 A | 9/2004 |
| MX | PA03006874 A | 9/2004 |
| MX | 225663 B | 1/2005 |
| MX | 226292 | 2/2005 |
| MX | PA03010507 A | 7/2005 |
| MX | PA05011725 A | 5/2006 |
| MX | 06011286 | 3/2007 |
| MX | 246862 B | 6/2007 |
| MX | 2007006441 A | 8/2007 |
| MX | 265247 | 3/2009 |
| MX | 284569 B | 3/2011 |

OTHER PUBLICATIONS

Communication pursuant to Article 94(3) EPC issued in European Patent Application No. 20212737.9 dated Jul. 11, 2023.

\* cited by examiner

LYMPHATIC SYSTEM TRACKING

FIELD

The disclosure relates to surgical imaging systems, and more particularly, to systems and methods for assisting a clinician performing surgery on lymphatic and other luminal structures.

BACKGROUND

As technology has advanced, surgeons have largely replaced classical open surgical techniques with minimally invasive techniques such as laparoscopic and thoracoscopic surgery in an effort to minimize trauma to surrounding tissue, reduce pain, reduce scarring, and reduce the length of time a patient is required to stay in the hospital. Minimally invasive surgery, such as the thoracoscopic approach pioneered in the mid-19th century, involves the use of small incisions (from one to several), typically no larger than 3-10 mm. Originally performed using a cystoscope, advances in medical technology led to the development of specialized instruments for use in the thoracic cavity, such as a thoracoscope, to view anatomy within the thoracic cavity while performing the surgical procedure. In the late 20th century, Video Assisted Thoracic Surgery (VATS) was developed utilizing a fiber-optic endoscope to further reduce the size of incisions required to make the incision and to provide clearer, more defined images of the thoracic cavity.

In parallel with the advances in minimally invasive surgeries have come advances in in-situ imaging techniques. Employing these in-situ techniques, dyes, such as indocyanine or methylene blue, can be injected into the body. These dyes are typically injected into blood vessels and other luminal networks so that the blood vessel or other luminal network pathway can be observed when the dyes are excited by various wavelengths of infrared and near-infrared light.

While these technologies have led to improvements in surgical outcomes, improvements to the technology are always desirable.

SUMMARY

The disclosure is directed to a system and method that enables real-time visual examination of in vivo tissues and selective display of luminal networks lying beneath the surface of the tissues being examined.

In one aspect, this disclosure features a method of imaging tissue. The method of imaging tissue includes receiving white light images, receiving near infrared (NIR) images, storing the NIR images in memory, and detecting fluorescence in the NIR images. The method of imaging tissue also includes generating composite images including the white light images and NIR images in which the fluorescence is detected. The method of imaging tissue also includes displaying the composite images in a user interface.

In aspects, implementations of this disclosure may include one or more of the following features. The composite images may be formed of white light images captured at a time after the NIR images are received. The method may also include registering the white light images and the NIR images. The registration may be an electromagnetic-based registration. The registration may be an image-based registration. Detecting fluorescence may include determining which pixels in the NIR images change brightness at a rate faster than a threshold.

In another aspect, this disclosure features a system for imaging a patient. The system includes an endoscope including a white light source, a near infrared (NIR) light source, and at least one camera capable of capturing reflected white and NIR light. The system also includes a processor in communication with the at least one camera and configured to generate a white light video and an NIR video from the captured reflected white and NIR light. The system also includes a display in communication with the processor to selectively present a user interface including the white light video or the NIR video. The system also includes a memory having stored thereon an application which, when executed by the processor, causes the processor to detect fluorescence in the NIR video, generate a composite video including the white light video and the fluorescence detected in the NIR video, and display the composite video on the display.

In aspects, implementations of this disclosure may include one or more of the following features. The NIR video may be stored in memory. The application, when executed by the processor, may further cause the processor to register the NIR video to the white light video. The white light video registered to the NIR video may be captured after the detection of the fluorescence in the NIR video. The system may also include an electromagnetic (EM) field generator. The endoscope may include an EM sensor. The application, when executed by the processor, may further cause the processor to determine a position of the EM sensor in a field generated by the EM field generator. The application, when executed by the processor, may further cause the processor to perform image-based registration of the NIR video and the white light video. The displayed composite video may depict the white light video correlated to fluorescing pixels in the NIR video with an altered color. The application, when executed by the processor, may further cause the processor to correlate fluorescing pixels in the NIR video to pixels in the white light video. Detecting fluorescence in the NIR video may include determining which pixels in the NIR video change brightness at a rate faster than a threshold.

In another aspect, this disclosure features a method of identifying an area of interest in an endoscopic image. The method includes illuminating tissue with white light. The method also includes capturing reflected white light. The method also includes illuminating tissue with near infrared (NIR) light. The method also includes capturing fluorescence emitted by tissue infused with a fluorescent dye. The method also includes displaying the captured reflected white light as a white light video on a display. The method also includes storing the captured fluorescence as a video in a memory. The method also includes displaying the fluorescence video and the white light video on the display.

In aspects, implementations of this disclosure may include one or more of the following features. The fluorescence video may be registered to the white light video. The registration may be an image-based registration. A composite video including the white light video and fluorescence video may be generated and displayed such that the fluorescence may be observable in the white light video. The method may also include detecting pixels in the fluorescence video corresponding to pixels in the white light video. The method may also include displaying the white light video with the corresponding pixels having a changed color.

A further aspect of the disclosure is directed to a method of imaging tissue including steps of illuminating tissue with white light, capturing white light images, and illuminating tissue with near infrared (NIR) light. The method further includes detecting fluorescence emitted by tissue infused with a fluorescent dye, converting the detected fluorescence into a centerline of perfusion, and overlaying the centerline of perfusion onto the white light image. The method may include displaying a composite image of the white light image and the centerline of perfusion on a user interface. The centerline of perfusion may be determined from the rate of change of a detected position of detected fluorescence. The centerline of perfusion may be determined as a median of a plurality of vectors determined via image processing of multiple images in which fluorescence is detected. Further, the centerline of perfusion may be determined prior to a current white light video image on which the centerline of perfusion is overlaid. Still further, a current white light image and a prior white light image may be used to register a location of the centerline of perfusion in the current white light image.

BRIEF DESCRIPTION OF THE DRAWINGS

Various aspects and features of the disclosure are described hereinbelow with references to the drawings, wherein.

DETAILED DESCRIPTION

Figure 1:
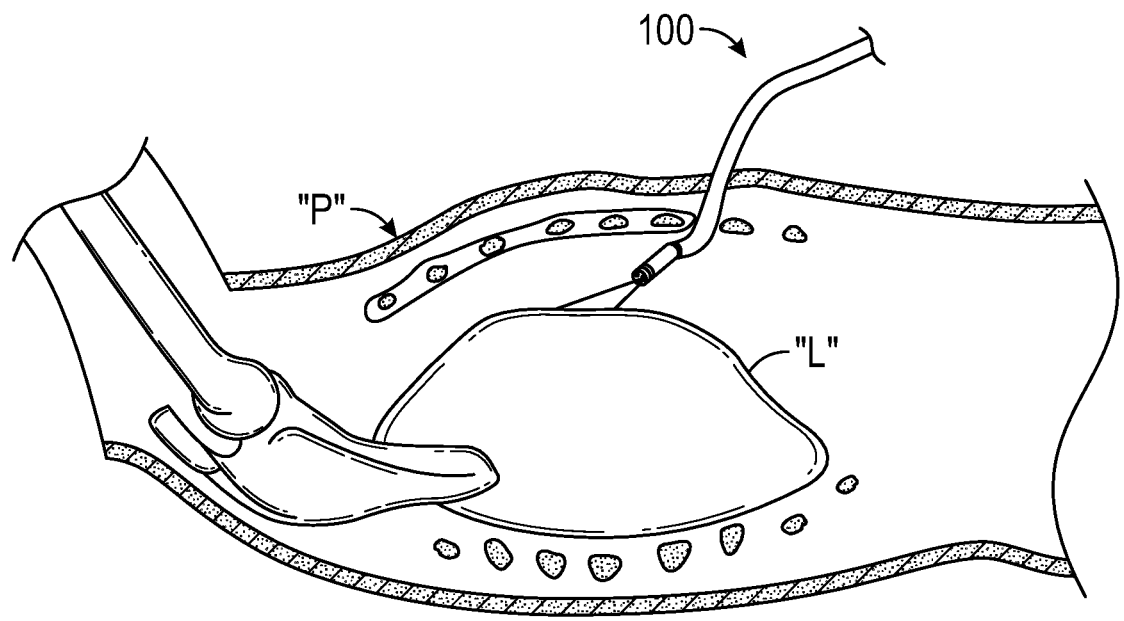
FIG. 1 depicts an endoscope inserted into a patient during a thoracic procedure.

The disclosure is directed to a system and method that enables real-time visual examination of in vivo tissues and selective display of luminal networks lying beneath the surface of the tissues being examined. FIG. 1 depicts an endoscope 100 inserted into the thoracic cavity of a patient (P) and used to image a surface of the patient's lungs (L) as might occur during a thoracic surgery.

Figure 2:
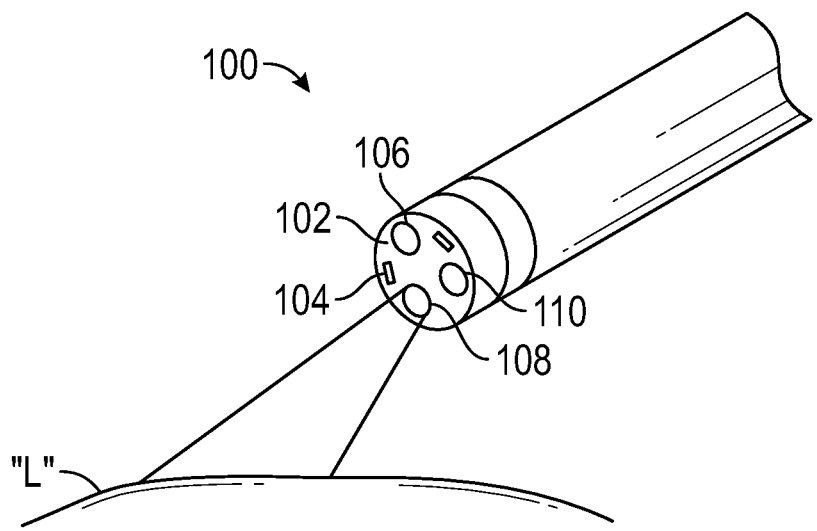
FIG. 2 depicts a distal portion of an endoscope in accordance with aspects of the disclosure.

Details of the endoscope 100 can be seen in FIG. 2, in which a distal surface 102 of the endoscope 100 includes a first light source 104, a first camera 106, a second light source 108, and a second camera 110. Although generally illustrated as being disposed in a circular configuration (i.e., disposed about the circumference of the distal surface 102), it is contemplated that each of the first and second light sources 104, 108 and the first and second cameras 106, 110 may be disposed in any suitable configuration allowing for their serial or in-parallel use.

The first camera 106 may be a white light optical camera such as a charge-coupled device (CCD) camera, a complementary metal-oxide-semiconductor (CMOS) camera, an N-type metal-oxide-semiconductor (NMOS) camera, or any other suitable white light camera known in the art. Similarly, the first light source 104 may be or may include a light emitting diode (LED) emitting white light, although any suitable light emitting device known in the art may be utilized (e.g., the first light source 104 may be the end of an optical fiber connected to a light source external to the patient). The second light source 108 may be a laser or another emitter of infrared (IR) or near infrared (NIR) light. Finally, the second camera 110 may be a CCD camera capable of detecting IR or NIR light. Other cameras capable of capturing IR or NIR light, either with or without filtering, are also contemplated in connection with the disclosure as are multi-spectral cameras such as those capable of capturing white light and NIR light using a single camera.

Figure 3:
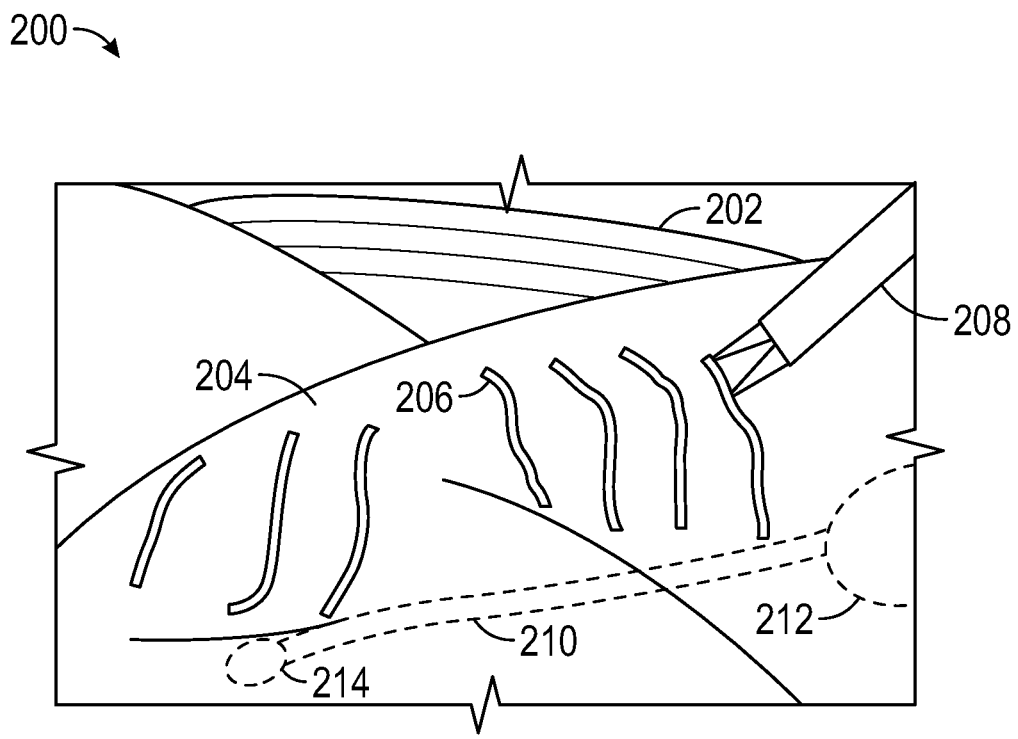
FIG. 3 depicts a white light image captured by the endoscope of FIG. 1 and displayed in a user interface in accordance with aspects of the disclosure.
Figure 4:
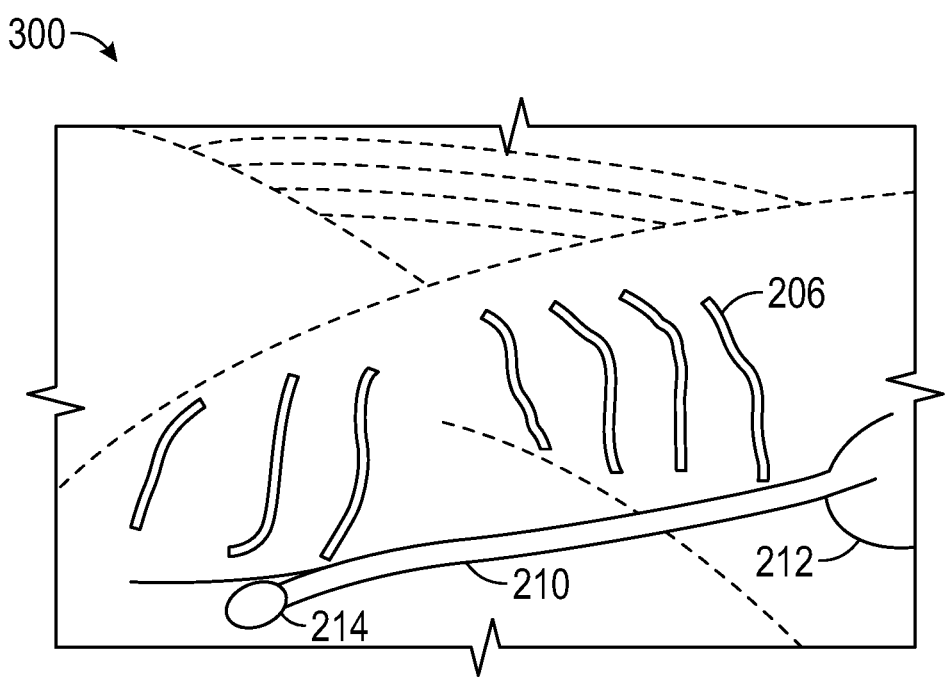
FIG. 4 depicts a near infrared image captured by an endoscope of FIG. 1 and displayed in a user interface.

Following insertion, as shown in FIG. 1, the first light source 104 and the first camera 106 are used for general navigation within the body of the patient. The white light emitted by the first light source 104 reflects off one or more tissues of the body and is captured by the first camera 106. The images from the first camera are displayed on a display, as shown in FIG. 3. FIG. 3 depicts a user interface 200 depicting the image captured by the first camera 106. The majority of the view may be taken up by one or more tissues and may include a number of tissue types, including connective tissue 202, organ tissues 204, blood vessels 206, and others. Also shown in the user interface 200 is a forceps 208, which can be used by the clinician to manipulate the one or more tissues. In the field of view, but not visible under white light visualization using the first camera 106, are hidden structures that lie below the tissue surface or are otherwise unobservable, such as lymphatic duct 210 which connects lymph nodes 212, 214 (FIG. 4).

To identify structures that are either below the surface of the tissue, or whose structure is not clearly distinguishable from a perspective above the surface of the tissue, various dyes may be employed. One such dye is indocyanine green (ICG) dye. When ICG dye is illuminated with certain frequencies of light in the IR or NIR range, the ICG fluoresces a green color that can be captured by a camera such as the second camera 108.

The capture of the NIR images can be triggered automatically or as directed by the clinician. The clinician can instruct or control the system to capture the endoscopic image using any suitable method of control available (e.g., footswitch, voice, assistant, or hand motion). Alternatively, the system can perform this task automatically by detecting sudden changes in the image. Automated detection accuracy can be improved through comparison with template images described below. When dyes such as ICG, which generate visible changes, are used the results are seen in the UI 200. The process of the dye diffusing through the tissue reveals anatomic detail, such as vasculature and parts of the lymphatic system. The pattern of diffusion provides information on the direction of flow within that structure. By capturing a video of the diffusion in the lymphatic or another luminal system, it is possible to show the clinician the network of connections (e.g., lymph nodes and lymphatic ducts) and to determine which connections are the sentinel nodes, thus allowing for more complete harvesting of such structures during cancer surgery.

With reference back to FIG. 2, to detect the location of blood vessels 206 that might be hidden or not abundantly apparent under white light visualization, ICG dye can be injected into the blood stream of the patient at a location proximate to an area of interest. As the blood having the ICG dye is transported through the blood vessels, the blood vessels will, for a time, appear distinct from the surrounding tissue when illuminated with an NIR light source. Thus, by illuminating the organ tissues 204 in FIG. 3 with NIR light from the second light source 108 and capturing the returned fluorescence from the ICG in the blood stream, blood vessels 206 will appear in the user interface 300, as shown in FIG. 4. Similarly, if a lymph node 212 is injected, diffusion through the lymphatic duct 210 to the lymph node 214 can be observed.

As shown in FIG. 4, the remainder of the tissue, which has not been infused with ICG dye, is much less visible or not visible at all. Instead, the UI 300 displays just those tissues through which the dye is diffusing. In FIG. 4, the blood vessels 206, the lymph nodes 212, 214, and the lymphatic duct 210 are clearly displayed. In one aspect, a clinician employing ICG and two imaging systems as described in FIG. 2, can toggle between UI 200 and UI 300 alternately so that the clinician can attempt to visualize the structures of the blood vessels 206 while performing most of their operation under white light visualization. Typically, the clinician will alternate between the two camera displays (FIGS. 3 and 4) to ensure that they are not about to damage certain tissues such as blood vessels, lymphatic ducts, or lymph nodes, or to make some other clinical determination during a procedure (e.g., that all desired lymph nodes 212, 214 connected via lymphatic duct 210 are removed). In addition, the UI 200 may display a composite of UI 200 and UI 300 as will be explained in greater detail below.

While the systems and methods described above are useful, dyes such as ICG have certain issues that impact the way they are used. First, some dyes tend to perfuse through the entirety of the tissues 202-206 as the dyes are passed through the circulatory system. Substantially all tissues receive blood from the circulatory system. As a result, after a period, the entirety of the tissue proximate to the tissue into which a dye has been injected will be perfused, thus saturating the captured images with fluorescence and rendering the fluorescence captured by the second camera 110 useless. Secondly, dyes dissipate relatively quickly and are only visible for a couple of minutes after injection. Many of these dissipating dyes also have a level of toxicity that makes it difficult or less than desirable to perform multiple injections of the dyes. These limitations force the clinician to act immediately or at least very quickly on the information gleaned from the use of the dyes and imaging the tissues.

Figure 5:
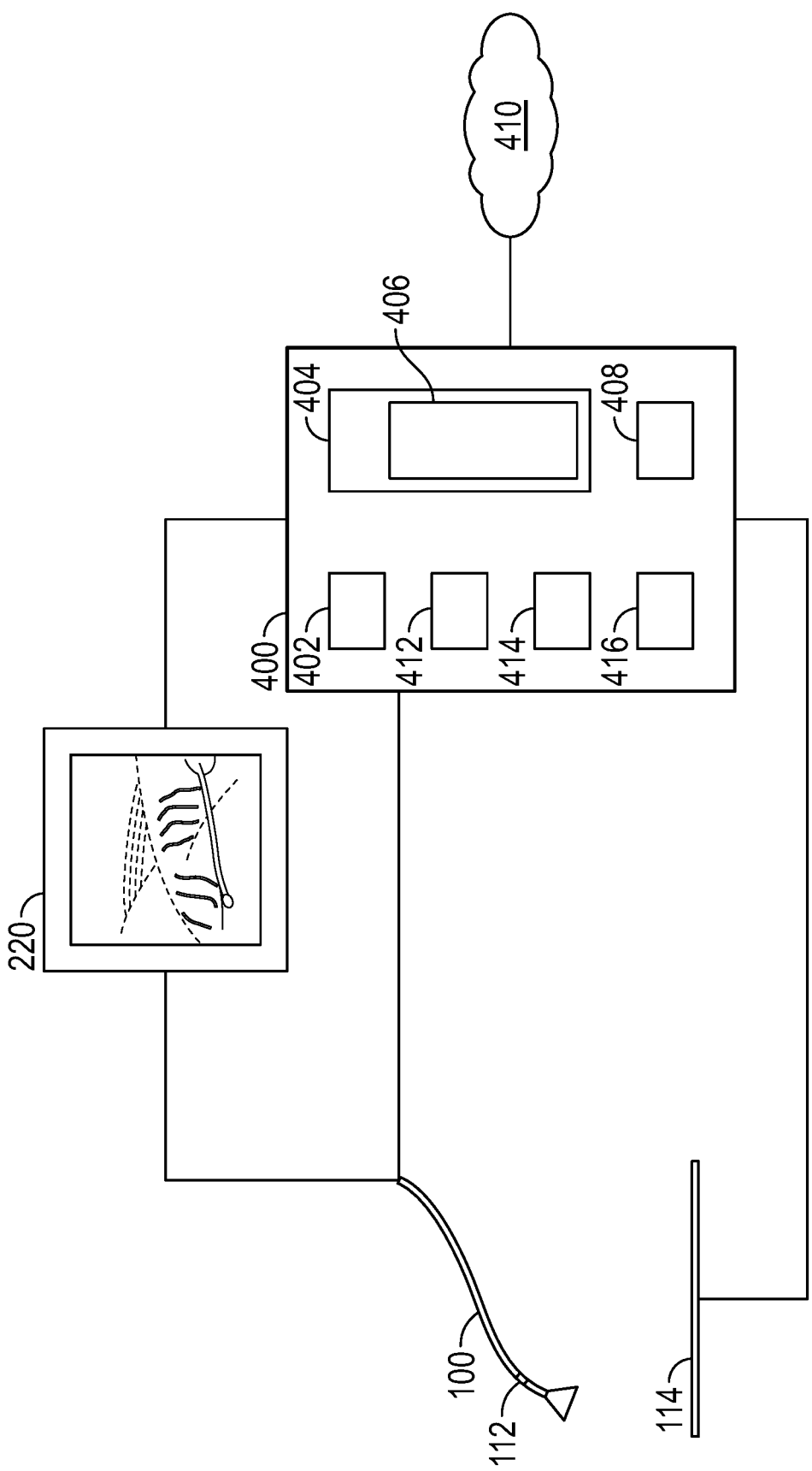
FIG. 5 depicts an imaging system in accordance with aspects of the disclosure.

FIG. 5 depicts a system employing a method of the disclosure. In FIG. 5, an endoscope 100 is connected to a display 220 to display user interfaces 200, 300 and separately connected to a workstation 400. The workstation 400 may be a desktop computer or a tower configuration with display 220 or may be a laptop computer or other computing device. The workstation 400 includes a processor 402 which executes software stored in the memory 404. The memory 404 may store video and other imaging data captured by the endoscope 100 or pre-procedure images from, for example, a CT scan. In addition, the memory 404 may store one or more applications 406 to be executed on the processor 402. Though not shown here, the display 220 may be incorporated into a head mounted display such as an augmented reality (AR) headset such as the HoloLens offered by Microsoft Corp.

A network interface 408 allows the workstation 400 to communicate with a variety of other devices and systems via the Internet. The network interface 408 may connect the workstation 400 via a wired or wireless connection. Additionally or alternatively the communication may be via an ad-hoc Bluetooth or wireless networks enabling communication with a wide-area network (WAN) and or a local area network (LAN). The network interface 408 may connect to the internet via one or more gateways, routers, and network address translation (NAT) devices. The network interface 408 may communicate with a cloud storage system 410, in which further image data and videos may be stored. The cloud storage system 410 may be remote from or on the premises of the hospital such as in a control or hospital information technology room. An input module 412 receives inputs from an input device such as keyboard, mouse, voice commands, etc. An output device 414 connects the processor 402 and memory 404 to a variety of output devices such as the display 220. Finally, the workstation 400 may include its own display 416, which may be a touchscreen display.

In at least one aspect, the endoscope 100 includes a location sensor such as an electromagnetic (EM) sensor 112 which receives electromagnetic signals from a field generator 114 generating three or more electromagnetic fields. One of the applications 406 stored in the memory 404 and executed by the processor 402 may determine the position of the EM sensor 112 in the EM field generated by the field generator 114. Determination of the position of the endoscope and the first and second cameras 106, 110 enables the registration of images. For example, as will be explained in greater detail below, a live white light image may be registered with an NIR image stored in memory. Though EM sensors are described above, other position sensors, such as ultrasound sensors, flex sensors, robotic position detection sensors, are contemplated within the scope of the disclosure.

In accordance with the disclosure, a method of utilizing a video of the dye diffusion is described herein. Rather than simply imaging the tissue so that it can be displayed while the clinician is performing the surgery, the injection of the ICG dye and its diffusion through the tissue is captured as a video. The captured video of the diffusion of the ICG dye through the tissue can be played back at any time by the clinician. This allows the clinician to observe the direction of the diffusion as well as the relative speeds of diffusion through different vessels. This video of the diffusion of the ICG dye can be played back at a suitable speed (e.g., either at normal speeds or at high speeds) so that the clinician can observe the locations of the blood vessels or other tissues such as the lymph nodes 212, 214 before the tissue becomes entirely perfused. This video may then be overlaid on the real-time white light images (FIG. 3) that are captured by the first camera 106 and displayed on the display 220.

In one aspect, the white light images are captured by the first camera 106. The lymph node 212 or a sentinel node upstream from the lymph node 212 may be injected with the ICG dye. The second light source 108 and the second camera 110 may be selected and, by observing fluorescence of the ICG dye when under NIR illumination, the location of the lymph nodes 212, 214 may be determined. Importantly, the direction of travel from the lymph node 212 to the lymph node 214, can be observed. The direction of travel through the lymphatic system can be an important factor in determining the likely spread of cancer and other diseases. Thus, by observing the direction of travel, if the lymph node 214 is down stream from the lymph node 212, then a clinical determination may be made as to whether lymph node 214 should be removed. This determination is usually based on the proximity of the lymph node 214 to a cancerous lymph node or a sentinel node. In addition, a more complete map of the lymph node tree can be developed and stored in the memory 404.

Because a video of the lymphatic system or at least a portion of the lymphatic system is stored in the memory 404, the clinician can reference the video at any time. In accordance with one aspect of the disclosure, one or more registration points are identified either automatically or by the user in the white light video, which may be captured simultaneously with the NIR video. Since the NIR video and the white light video may be captured simultaneously (or at alternating times which occur at a high speed), by identifying a location of a structure in one video, that same structure can be located in the other video. This allows the data from one, e.g., the position of the lymph nodes 212, 214 and the lymphatic duct 210 connecting them, to be accurately displayed as an overlay on the white light video.

Further, by identifying registration points, image recognition techniques can be employed to allow the system to display the lymph nodes 212, 214, even upon movement of the endoscope 100 where one of the lymph nodes 212, 214 may no longer be observable using the white light camera 106. In such a scenario, a representation of the lymph node behind the intervening tissue may still be displayed. This may be very useful when, for example, navigating the endoscope 100 within the patient. Once the registration points are in the view of the endoscope 100, the location of the lymph nodes 212, 214 will be known and can be displayed in the white light images on display 220.

Alternatively, image recognition techniques make it possible to determine which pixels in the image of the NIR camera are detecting fluorescence. Because the field of view of the white light first camera 106 and the NIR camera 110 are known, the location of the lymph nodes 212, 214 and the lymphatic duct 210 connecting them can be observed. The pixel data can then be transferred to, overlaid on, or otherwise applied to the white light images, so that the corresponding pixels of the white light images in the substantially same field of view are highlighted to display the locations of the lymph nodes 212, 214. In practice, this may only be performed for those lines of pixels that are changing at a rate of change that is greater than a set threshold. This limits the growth of the pixelized areas in the white light images by applying, to the white images, just the pixel data of the lymph nodes and lymphatic vessels, and not the pixel data of the surrounding tissue into which the ICG dye will ultimately, but more slowly, diffuse. Though described with respect to the lymph system, the same could be done with the blood vessels in the area. These and other methods of utilizing the data received from the first camera 106 and the second camera 110 are described in greater detail below.

Figure 6:
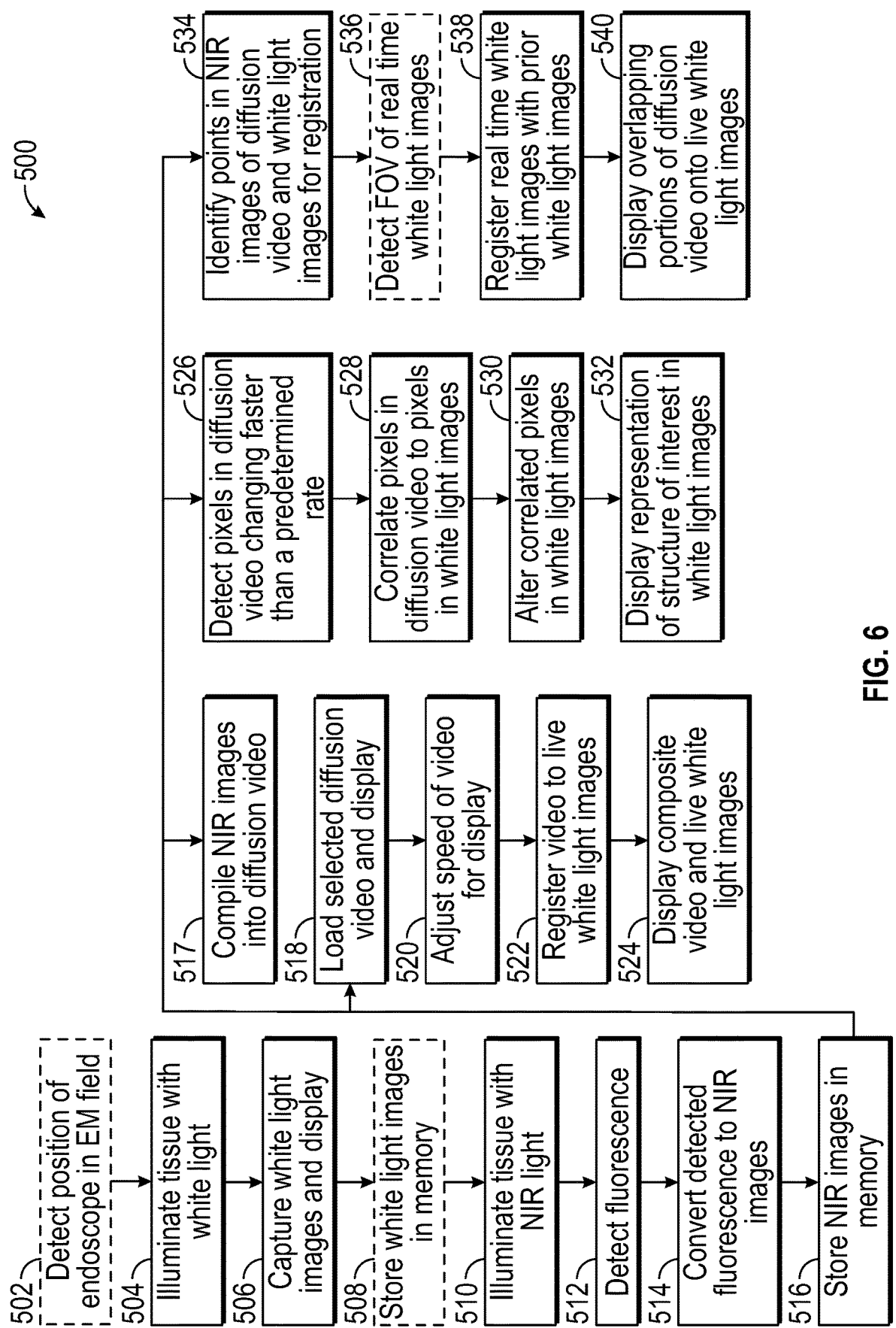
FIG. 6 is a flow chart of an endoscopic imaging procedure in accordance with the disclosure.

FIG. 6 shows a flow chart 500 of a method for use by the system displayed in FIG. 5. Following insertion of an endoscope into, for example, the thoracic cavity as shown in FIG. 1 the system may optionally detect the position of the endoscope at step 502, The position of the endoscope 100 may be detected using the EM sensor 112 and the EM field generator 114. Those of skill in the art will recognize that EM detection is not necessarily required for use with the instant imaging techniques and other techniques such as image matching to pre-procedural images (e.g., CT images) or three-dimensional models derived from such images, as well as two dimensional images generated from the 3D images may be employed to determine the position of the endoscope relative to the tissue being examined. Once inserted, the endoscope 100 may be navigated within the patient. While navigating, the tissue is illuminated with white light at step 504 and the white light reflects off the tissue and other structures and white light images are captured at step 506 and can be stored in memory 404 at step 508 and may be simultaneously displayed on display 220. An application 406 stored in memory 404 may store the images in a fashion such that they can be replayed sequentially in a white light video. The white light images permit the clinician to observe the tissue and visually inspect and identify locations for further analysis. Once positioned at a location where detection of areas of interest (e.g., lymph nodes, blood vessels, etc.) is desired, dye may be injected into the tissue at a clinically appropriate position such that the dye will diffuse through the area of interest. Once injected, the area of interest is illuminated with NIR light at step 510. As noted above, the dye, when excited by NIR light, fluoresces. The fluorescence can then be detected at step 512 via the second camera 110. The detected fluorescence is converted into NIR images at step 514 and saved in memory 404 at step 516. These images can be saved at a frequency allowing for the observation of the dye as it diffuses through an area of interest. The frequency may be, for example 15, 30, 45, 60, 120 images per second, as well integer values therebetween. The NIR images may be compiled into a video so that the diffusion may be observed over time. The diffusion video may also be saved in memory 404 at step 517.

The acquiring of both NIR and white light images may occur in an alternating fashion or simultaneously. The user may determine which of the images to display on the display 220. This may be the live white light images, the live NIR images, or the NIR diffusion video stored in the memory 404. If it is a diffusion video stored in memory 404 that is desired to be displayed, the appropriate diffusion video may be selected by a clinician and the diffusion video may be loaded into an application 406 at step 518 for display. In addition, at step 520, a speed of the video may be adjusted in response to a request received from a user. Increasing the speed of the video can be useful to the clinician in clearly and quickly outlining where areas of interest (e.g., blood vessels, lymph nodes, lymphatic ducts, etc.) are located. This can allow a clinician to play the video forwards and backwards, and at varying rates of speed to ensure that the locations of the areas of interest are well understood. Knowledge of these areas can assist the clinician when determining which structures to cut, avoid, biopsy, or remove as necessary.

The video, as adjusted at step 518 may be displayed on the display 220. The presentation of the video may be as a picture-in-picture format allowing the clinician to observe both the video and the real-time white light images received from the endoscope. Alternatively, the video and the real-time white light images may be displayed side-by-side and/or having approximately the same size.

In a further aspect, where the field of view of the white light images captured by the endoscope at least partially aligns with the field of view of the video stored in memory, a registration of the video and the live images may be undertaken at step 522. Following registration, the diffusion video (or an individual NIR image) may be displayed as an overlay on the real-time white light video (or an individual image in the white light video) at step 524. This overlay of the NIR video, in which only those portions of the field of view (FOV) which fluoresce can be readily observed, results in a composite video of the NIR video and the white light video viewable on the display 220. In this way, the NIR video can be used to identify structures in the FOV of the white light video. As the FOV of the endoscope changes with its movement, those portions of the white light video which are no longer aligned with the FOV of the NIR video may no longer be depicted as a composite video, but rather only the white light video is displayed. This may be considered an indicator to the clinician to move the endoscope back to a location where the NIR video clearly reveals the locations of the areas of interest.

Additionally, or alternatively if any portion of the structures of the NIR video are still in the FOV of the white light, the white light video may be warped in order to fit the portion of the NIR video in the FOV of the white light video. In embodiments with EM sensor 112 collecting position data of the cameras 106, 110 of the FOV a calculation can be made to determine the amount of foreshortening, rotation, and other warping to perform.

If a 3D endoscope is used, the coordinates of the area of interest may be extracted directly from the scanned model annotated with any additional information extracted from the images such as luminal network connection data and fluid flow direction as described for lymph nodes above. This additional data may be stored in the memory 404 and available for use by the clinician as the endoscope is returned to one or more stored coordinate positions.

In accordance with another aspect of the disclosure, an application 406 stored in memory 404 can be employed to analyze the NIR images captured by the endoscope 100 at second camera 110. This may occur in real time as the images are captured or may involve processing the video stored in memory 404. The images are analyzed at step 526 to determine which pixels in the NIR images of the diffusion video are experiencing a change in brightness or illuminance (typically measured in lux or foot-candle). The change in brightness is a result of the NIR light from the second light source 108 illuminating the ICG dye that is diffusing through the area of interest.

Because the NIR images may be captured substantially simultaneously with the white light images, the images are necessarily registered with one another. Because of the registration of the simultaneous capture of the images, by determining which pixels in the NIR images are changing from not fluorescing to fluorescing, an indication of the location of areas of interest can be made. The rate of the change is relevant to the identification of the larger vessels carrying the dye. Blood vessels and other luminal structures greater than a certain diameter allow the dye to pass through relatively quickly and thus change from not fluorescing to fluorescing quickly. By detecting this rate of change, and only identifying those pixels that change at a rate greater than a threshold, those pixels that are slower to change can be eliminated from further processing and thus prevent the saturation described above.

Once the pixels that are changing at a rate greater than a predetermined rate are identified, these pixels can then be correlated to the same pixels in the FOV of the white light images at step 528. Once the pixels are identified in the white light images, these pixels can then have their brightness or color changed such that the area of interest is revealed in the white light images at step 530 and this altered white light image can be displayed at step 532.

As noted herein above, registration of the NIR images and the white light images is a useful feature in enabling the data derived from the NIR images to be observed in the white light images. One form of registration requires the use of the EM sensor 112 and the field generator 114. A detected position of the EM sensor 112 in the EM field can be correlated to each frame of both the white light videos and the NIR videos. With reference to the position data of the NIR images, once the position data for each frame in the NIR video depicting the perfusion of the dye through the area of interest is determined, the NIR video data can be made available and displayed in the white light images as described above using the correlation of the position of the NIR images with the white light images.

In addition to EM field position detection and registration, other forms of registration are also possible. For example, an application 406 stored in memory 404 may engage in image detection that identifies structures or other hard points in every image of the white light video at step 534. These hard points are also necessarily in the NIR images that are simultaneously captured, and as described above. As a result, the white light video images and the NIR video images are necessarily registered with one another. However, if use is to be made of the diffusion video at a later time (e.g., later in a long procedure, or even in a subsequent procedure), some form of registration is required. By identifying registration points in the white light video that was captured substantially simultaneously with the NIR video images, when these registration points are observed in subsequent white light video images, a correlation or registration can be performed between these later captured video images and the original white light video images.

The registration may include a step 536 of determining a FOV of the endoscope 100 and white light images captured by the endoscope. Registration of the real time white light images with the previously captured white light images necessarily also registers the previously captured NIR images to the current white light images at step 538, and thus the diffusion video with the real time white light images. In this way, either selectively or automatically, as new white light images are captured via the endoscope 100, the fluorescence observed in the NIR images of the diffusion video from the same FOV as the real-time white light video can be displayed on the display 220 at step 540.

Yet a further aspect of the disclosure is described with reference to FIGS. 7 and 8. In instances where displaying a previously acquired NIR video is challenging, or results in images that are less than entirely useful for a given case, an alternative may be employed.

Figure 7:
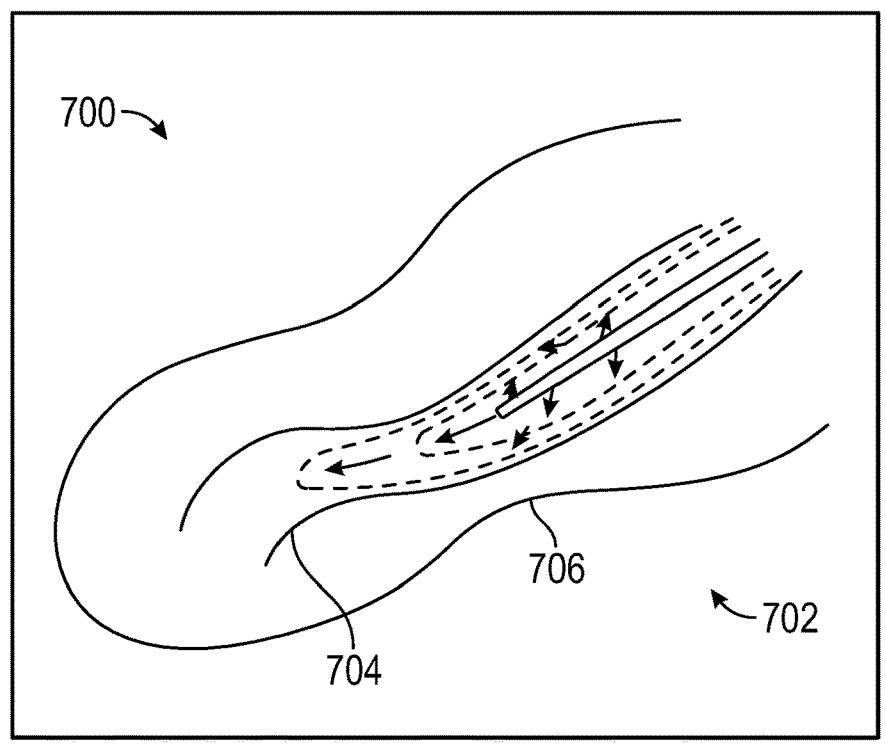
FIG. 7 depicts a NIR image captured by the endoscope of FIG. 1 in accordance with a further aspect of the disclosure.

In FIG. 7 an overlay 700 of three NIR images acquired at approximately the same location but at different times (e.g., frames of a video separated by 5, 10, 30 or more seconds) is displayed on a white light image 702. In FIG. 7 a vessel 704 is depicted within tissue 706. Fluorescent dye transits the vessel 704 and perfuses the surrounding tissue. A first image of the overlay 700 depicts the flow of the fluorescent dye into the vessel 704 at a first time (solid line). The second (short dashed lines) and third (long dashed lines) images of the overlay 700 depict the fluorescent dye as it traverses the vessel 704 and perfuses into the surrounding tissue. Because the time between images is known, an image analysis of the respective images can be undertaken to determine the perfusion vectors 706 in any given direction. The difference in location of detected fluorescence within successive images or frames provides a vector of movement of the fluorescent dye within the vessel 704 and tissue 706. These vectors can be used to determine a flow path of the fluorescent dye through the vessel 704 and tissue 706. From the vectors the flow path may be determined from any single vector for an image acquired at a specific time. The vectors also enable the determination of a centerline of the perfusion of the fluorescent dye. 24. The centerline of perfusion may be determined as a median of a plurality of the vectors determined via image processing of the plurality of images.

Figure 8:
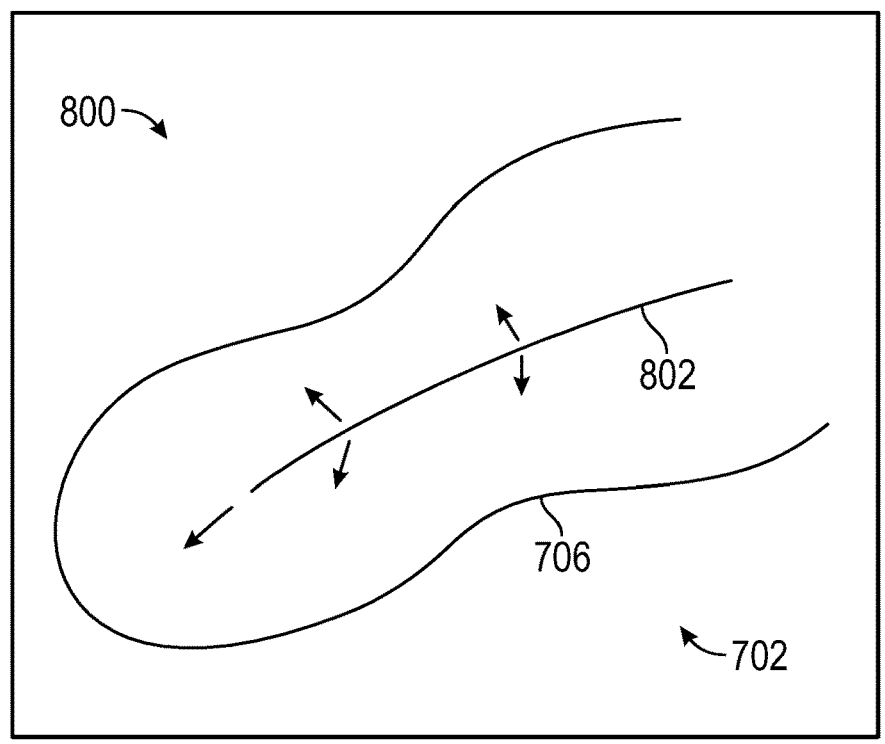
FIG. 8 depicts an overlay of a calculated centerline of a target of interest derived from the NIR image of FIG. 7.

FIG. 8 depicts an overlay 800 on a white light image of the centerline of the perfusion 802 of the fluorescent dye, calculated from the vectors of fluorescent dye perfusion. In some instances, the depiction of the centerline of the perfusion 802 requires less processing power, and also provides a generally clearer field of view of the white light image as compared to overlaying an NIR video. Still further, that centerline data may have a longer lifespan of relevance to the clinician as the location of the vessel may remain a relevant consideration long after the fluorescent dye has saturated the entirety of the tissue 706 or axis requires less computer resources to maintain as compared to the video memory and has longer temporal user value compared to rate threshold information. Further the determined centerlines may be combined from several NIR videos (i.e., multiple images from separate NIR videos) to create a more complete knowledge of the structure of interest.

As a result of the processes above, an area of interest can be tracked continually during the remainder of the surgery. For example, image recognition techniques may be used to follow the anatomy during the dissection and resection process as parts of the anatomy are split into smaller sections or removed entirely. At times, the area of interest may become obscured or covered by other anatomy or instruments. Whether using EM registration and position detection or image-based registration, the system may recover the tracking process when the common landmarks described earlier return into view.

In one aspect the clinician may at any time toggle on an anatomy tracking feature to see where the highlighted anatomy has moved to or if it still exists. In the case of lymph node resection, the clinician may have marked an area on the display that is intended to be removed. The system of the disclosure can track the area of interest and can notify the surgeon when the tracked area has been entirely removed. When sentinel lymph nodes are removed, the surgeon can be alerted as to the presence of connected lymph nodes that should be considered for removal as well While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects.

What is claimed is:

1. A method of imaging tissue comprising:
    illuminating tissue with near infrared (NIR) light;
    detecting fluorescence from the tissue;
    converting detected fluorescence to NIR images of the tissue;
    compiling the NIR images of the tissue into an NIR video;
    identifying pixels in the NIR video changing fluorescence over a duration of the NIR video at a rate in excess of a threshold, wherein the changing fluorescence in excess of the threshold is indicative of a location of a luminal network within the tissue;
    storing the NIR video and the identified pixels in a memory;
    capturing live white light images of the tissue;
    identifying pixels in the live white light images that correspond to the identified pixels in the NIR video;
    generating composite images from the live white light images, wherein the identified pixels in the white light images that correspond to the identified pixels in the NIR video are highlighted; and
    displaying the composite images in a user interface.

2. The method of claim 1, further comprising registering the live white light images and the NIR video.

3. The method of claim 2, wherein the registration is an electromagnetic-based registration.

4. The method of claim 2, wherein the registration is an image-based registration.

5. The method of claim 1, wherein the luminal network is one of blood vessels or lymphatic ducts.

6. A system for imaging a patient, comprising:
    an endoscope including a white light source, a near infrared (NIR) light source, and at least one camera capable of capturing white light images of tissue and detecting fluorescence of the tissue;
    a processor in communication with the at least one camera and configured to generate a white light video from the captured white light images and a diffusion video of the detected fluorescence;
    a display in communication with the processor to selectively present a user interface including the white light video or the diffusion video; and
    a memory having stored thereon an application which, when executed by the processor, causes the processor to:
    convert detected fluorescence into NIR images of the tissue;
    compile the NIR images into a diffusion video;
    identify pixels in the diffusion video changing fluorescence over a duration of the diffusion video at a rate in excess of a threshold, wherein the changing fluorescence in excess of the threshold is indicative of a location of a luminal network within the tissue;
    store the diffusion video in the memory;
    capture live while light images of the tissue;
    identify pixels in the live white light images of the tissue that correspond to the identified pixels in the diffusion video;
    generate a composite video from the live white light images of the tissue, wherein the identified pixels in the live white light images that correspond to the identified pixels in the diffusion video are highlighted; and
    display the composite video on the display.

7. The system of claim 6, wherein the diffusion video is stored in memory.

8. The system of claim 6, wherein the application, when executed by the processor, further causes the processor to register the diffusion video to the live white light images.

9. The system of claim 8, further comprising an electromagnetic (EM) field generator,
    wherein the endoscope includes an EM sensor, and
    wherein the application, when executed by the processor, further causes the processor to determine a position of the EM sensor in a field generated by the EM field generator.

10. The system of claim 8, wherein the application, when executed by the processor, further causes the processor to perform image-based registration of the diffusion video and the white light images.

11. The system of claim 10, wherein the displayed composite video depicts the identified pixels with an altered color.

12. The system of claim 6, wherein the luminal network is one of blood vessels or lymphatic ducts.

13. A method of identifying an area of interest in an endoscopic image comprising:
    illuminating tissue with near infrared (NIR) light;
    detecting fluorescence emitted by tissue infused with a fluorescent dye at a first time;
    converting the detected fluorescence to NIR images and storing them in memory;
    compiling the NIR images as a diffusion video, wherein the diffusion video depicts the diffusion of the fluorescent dye through the tissue;
    identifying pixels in the diffusion video changing fluorescence over a duration of the diffusion video at a rate in excess of a threshold, wherein the changing fluorescence in excess of the threshold is indicative of a location of a luminal network within the tissue;
storing the diffusion video in memory;
illuminating tissue with white light;
capturing live white light images;
identifying pixels in the live white light images that correspond to the identified pixels in the diffusion video;
generating a composite video from the live white light images, wherein the identified pixels in the live white light images that correspond to the identified pixels in the NIR video are highlighted; and
displaying the composite video on the display.

14. The method of claim 13, wherein the diffusion video is registered to the white light images.

15. The method of claim 14, wherein the registration is an image-based registration.

16. The method of claim 13, further comprising:
displaying the identified pixels of the live white light images with a changed color.

17. The method of claim 13, wherein the luminal network is one of blood vessels or lymphatic ducts.

* * * * *